United States Patent [19]
Wood et al.

[11] Patent Number: 5,997,906
[45] Date of Patent: Dec. 7, 1999

[54] COATED SODIUM PHOSPHATE BOWEL CLEANSER

[75] Inventors: Thomas G. Wood, Lynchburg, Va.; Robert McCrimlisk, Sparta; Kenneth G. Sarnowski, Mahwah, both of N.J.

[73] Assignee: C.B. Fleet Company, Inc., Lynchburg, Va.

[21] Appl. No.: 08/970,089

[22] Filed: Nov. 13, 1997

Related U.S. Application Data

[60] Provisional application No. 60/030,870, Nov. 13, 1996.

[51] Int. Cl.$^6$ ............................... A61K 31/74; A61K 9/36
[52] U.S. Cl. ..................... 424/494; 424/490; 424/489; 424/464; 424/78.01; 514/892
[58] Field of Search ................................ 424/464, 78.01, 424/892, 489, 490, 494

[56] References Cited

U.S. PATENT DOCUMENTS

| | | |
|---|---|---|
| 4,999,200 | 3/1991 | Casillan . |
| 5,498,425 | 3/1996 | Wood et al. . |
| 5,616,346 | 4/1997 | Aronchick . |

*Primary Examiner*—Thurman K. Page
*Assistant Examiner*—Brian K. Seidleck
*Attorney, Agent, or Firm*—Nikaido Marmelstein Murray & Oram, LLP

[57] ABSTRACT

A sodium phosphate bowel cleansing composition which has improved taste over conventional sodium phosphate compositions. The composition comprising free flowing monobasic sodium phosphate and dibasic sodium phosphate powders or crystals which have been coated with at least one edible grade film forming polymer such as hydroxypropyl-methyl cellulose or polyethylene glycol.

24 Claims, No Drawings

COATED SODIUM PHOSPHATE BOWEL CLEANSER

This application claims the benefit of U.S. Provisional Application No. 60/030,870, filed Nov. 13, 1996.

BACKGROUND OF THE INVENTION

The movement of nutrients, wastes, electrolytes, and water through the human intestines depends on the proper balance of absorption and secretion of water and electrolytes by the intestinal epithelium. Various pathogens, physical conditions and drugs can affect this balance or affect intestinal motility which can result in constipation. Laxatives can be used to treat constipation by promoting defecation. In addition, laxatives are useful for bowel clearance before radiological examination, colonoscopy, endoscopic examination, surgery or childbirth.

There are three basic mechanisms of laxative action. The first mechanism is the retention of fluid in colonic contents by the hydrophilic or osmotic properties of the laxative compositions. The second mechanism is a decrease in the absorption of water and NaCl by acting directly or indirectly on the colonic mucosa. The third mechanism of action is an increase in the intestinal motility, which causes decreased absorption of water and salt due to the increased transit time.

There are several different types of laxatives including dietary fiber and bulk-forming laxatives, stimulant laxatives, and saline and osmotic laxatives. Commonly used laxative products include castor oil, magnesium citrate, bisacodyl, PEG-electrolyte lavage and sodium phosphate. PEG-Lavage and sodium phosphate are the most commonly used products for colon cleansing prior to endoscopic examination.

The present sodium phosphate composition is an oral saline laxative and bowel cleanser. Saline laxatives are poorly and slowly absorbed and act by their osmotic properties in the luminal fluid. A commonly used oral saline laxative is "FLEET PHOSPHO-SODA" (21.6 g monobasic sodium phosphate and 8.1 g dibasic sodium phosphate in 45 ml of a stable buffered aqueous solution). This product has been found by most patients to have an unpleasant taste despite the addition of flavorings. In addition, some patients become nauseated and are affected by the slight electrolyte imbalance from using this product. In view of these problems, the object of the present invention is to provide a sodium phosphate bowel cleansing composition which has a pleasant taste and preferably binds ions to reduce the amount of electrolyte shift caused by the absorption of ions from the composition.

Though powdered pharmaceuticals may have been coated to mask taste in the past, the coating of sodium phosphate powders or crystals presents unique difficulties in that these compounds are highly ionic inorganic salts which are administered in larger amounts than most pharmaceuticals and require prolonged contact with water in a suspension. In view of this, the coatings which are used must have pores which are small enough to prevent the migration of ions through the coating and the coatings must be usable in amounts sufficient to coat large quantities of powder without adversely affecting the desired pharmacological effect. The present invention solves these problems allowing the production of a sodium phosphate bowel cleansing composition which has improved taste and retains the desired pharmacological effect.

SUMMARY OF THE INVENTION

The present invention relates to a bowel cleansing composition which overcomes the prior art problems of unpleasant taste. The present bowel cleansing composition contains a mixture of monobasic sodium phosphate and dibasic sodium phosphate free flowing powders or crystals which have been coated with an edible grade film forming polymer. The coating may be selected to attract sodium and/or phosphate ions, thus reducing the electrolyte shift after oral ingestion (i.e. a nonabsorbable coating can be used which attracts and binds ions thereby preventing the ions from being absorbed). Flavorings and dyes can be added to the composition to further improve the taste and appearance of the composition.

DETAILED DESCRIPTION OF THE INVENTION

The present invention is an improvement of a commonly used sodium phosphate saline laxative. In the present invention, free flowing phosphate powders or crystals are coated with a film forming polymer such as hydroxypropylmethyl cellulose (HPMC). Control release beads could also be made with the phosphate layered on a bead center and then coated with the film forming polymer. The phosphate can be coated with a pH dependent coating which is designed to release in the low pH of the stomach.

The phosphate powders of the present invention can be coated with any edible grade film forming polymer. The polymeric coating should be relatively impervious to passage of the sodium phosphates during passage through the patient' mouth. These polymers include gelatin, vegetable oils, natural polymers, starches, sugars, fats, paraffins, phospholipids, polyethylene glycol (PEG), and acrylic acid esters. Examples of preferred coating materials are HPMC E15, premium grade, which meets USP, Food Chemicals Codex, Kosher Certification and FDA Regulations for food and drugs; and standard pure food and drug paraffin. The coating can be selected to have additional properties such as binding sodium and/or phosphate ions (thereby reducing any electrolyte shift) and/or the coating may be nonmetabolizable. HPMC is an example of such a coating. The coating is applied in a layer sufficient to mask the taste of the phosphate powders and is substantially impervious to the aqueous solution in which the coated powder is suspended prior to administration. The coating can be applied by a variety of processes including but not limited to fluidbed processing, pan coating, spray dry coating, roller coating and dip coating.

The present invention contains sodium phosphate, preferably both monobasic and dibasic sodium phosphates, in an amount which produces between 200–1000 Mosmols per adult cleansing dose (Mosmols are a measure of osmotic strength). A dose of the present composition preferably contains the coated equivalent of 18.8 g uncoated $NaH_2PO_4$ anhydrous, which is about 22.56 g of coated $NaH_2PO_4$ anhydrous; and the coated equivalent of 4.3 g uncoated $Na_2HPO_4$ anhydrous, which is about 4.73 g of coated $Na_2HPO_4$ anhydrous; in 45 mls of a stable buffered aqueous solution. The monobasic and dibasic phosphates can be mixed prior to coating or can be coated individually and then mixed. The dibasic and monobasic phosphate crystals preferably have a particle size of between 10 and 200 mesh (i.e. the particles pass through a screen with 10–200 openings per inch) which results in a coated product which has a particle size of between 10 and 200 mesh.

Prior to administration, the dry coated powder is mixed with an aqueous solution. The weight ratio of the powder to the aqueous solution is between 1:1 to 1:1000.

The following examples are for illustrative purposes and are not intended to limit the scope of the present invention.

Minor modifications of the exemplified procedures will be obvious to those of skill in the art.

EXAMPLE 1
Coating the Phosphate Powders

A 10.0% solids solution of HPMC is prepared by dispersing 112.5 g of HPMC in 375 mls of purified water at 80–90° C. Once the HPMC is dispersed in the warm water, 762 mls of cool purified water are added.

To prepare the phosphate powders, 600 g of uncoated free flowing monobasic sodium phosphate powder is added to a fluidbed processing bowl and the bowl is positioned into the fluidbed processor. The processor is turned on causing the phosphate to be suspended in a heated (80–120° C.) air stream of 500–900 CFM. Once the phosphate is heated to a product temperature of 55–65° C. the HPMC solution prepared above is applied. The HPMC solution is applied by a controlled pumping system through an air atomized nozzle. The product temperature is maintained at 55–65° C. during the entire coating process. After the HPMC solution is applied the pumping system is turned off and the coated phosphate powder is dried to a moisture level of less than 1.0% $H_2O$. After the coated phosphate powder is dried, melted paraffin is sprayed on the coated phosphate powder until a ratio of between 1–10% w/w is obtained. During the spraying of the paraffin, the atomization air is heated 100°±15° C. The final product is removed from the fluid bed processor and classified through a 10 mesh Sweco screen to remove any oversized particles. In the coated product, the phosphate powder is coated with 10.0% (±7) HPMC by weight and 5.0% ±1% paraffin. The coating is between 2–40% by weight of the phosphate.

The coated dibasic sodium phosphate is prepared by substituting 7550 g of uncoated free flowing dibasic sodium phosphate for the monobasic sodium phosphate in the above process. Thus, 7550 (of uncoated free flowing dibasic sodium phosphate powder is added to a fluidbed processing bowl and the bowl is positioned into the fluidbed processor. The processor is turned on causing the phosphate to be suspended in a heated (80–120° C.) air stream of 500–900 CFM. Once the phosphate is heated to a product temperature of 55–65° C. the HPMC solution prepared above is applied. The HPMC solution is applied by a controlled pumping system through an air atomized nozzle. The product temperature is maintained at 55–65° C. during the entire coating process. After the HPMC solution is applied the pumping system is turned off and the coated phosphate powder is dried to a moisture level of less than 1.0% $H_2O$. The dibasic sodium phosphate is not coated with melted paraffin.

EXAMPLE 2
Preparation of a Dry Coated Sodium Phosphate Composition 24.89 g HPMC coated monobasic sodium phosphate 4.77 g HPMC coated dibasic sodium phosphate The coated monobasic and dibasic sodium phosphates are mixed and then stored as a dry composition.

EXAMPLE 3
Preparation of a Single Administration Dose

The dry coated sodium phosphate composition prepared in example 2 is suspended in 45 mls of water immediately prior to administration to a patient.

EXAMPLE 4
Comparison of the Safety and Effectiveness of Various Sodium Phosphate Preparations In this study, the bowel cleansing effectiveness, ease of consumption, side effects, and safety of sodium phosphate, normal 45 cc dose (Group I), reduced 30 cc dose sodium phosphate (Group II), coated sodium phosphate (Group III), and coated sodium phosphate and powder PEG 3350 (Group IV) were investigated. Sixty (60) patients undergoing colonscopy who met the inclusion/exclusion criteria participated. The inclusion criteria included patients who 1) were scheduled for elective outpatient colonscopy, and 2) were men & non-pregnant women, aged 18 years or older, who signed an institutional review board (IRB) approved written informed consent. Criteria for excluding patients from the study were patients with 1) Cr>2.0,2) symptomatic congestive heart failure, 3) known liver failure, 4) ascites, 5) patients who are pregnant or breast feeding, 6) patients with <100 # body weight, and/or 7) patients with acute myocardial infarction within the past 6 months.

After obtaining the informed consent, the patients were randomly assigned to one of four treatment groups. The subjects were given written instructions for use of the bowel cleansing product.

The subjects completed a one page questionnaire after taking the cleansing preparation and before colonoscopy at Martha Jefferson Hospital. The questionnaire consisted of rating difficulty with drinking prep and side effects.

The patients had a blood sample (Chem 21) drawn twice—once 3–7 days before the colonscopy in the office of Charlottesville Gastroenterology Associates (or at Martha Jefferson Hospital by prior arrangement) and then once immediately prior to colonoscopy at Martha Jefferson Hospital.

The colonoscopist completed the preparation study sheet and was blinded to the type of patient preparation.

As shown table 1, listing the patient questionnaire results, Group 1 (two doses of 45 ml sodium phosphate) had the largest total for side effects. The side effect scoring is 0=none, 1=mild, 2=moderate and 3=severe. Groups 2 through 4 showed less nausea, vomiting and abdominal bloating than group 1. Group 2 showed less trouble drinking than groups 1, 3 and 4. Group 1 showed substantially more anal irritation and weakness or faint feeling than the other groups.

Table 2, colon cleansing, shows that group 1 cleansed slightly better than the rest of the groups but not statistically significant.

Tables 3–6 show the difference of each of four electrolytes before and after dosing with various presentations of sodium phosphate. Phosphorus is the only meaningful data, due to the extreme scatter of the other data. Group 1 patients showed an increase in phosphorus absorption which amounted to about 50% more as compared to groups 2, 3 and 4. The increase is statistically significant at the 99% confidence level. Group 4 showed less phosphorus absorption than groups 2 and 3 but the difference was not statistically significant.

Table 7 is a list of the directions of the change in other values in the CHEM 7 and CHEM PROFILE.

This study shows that the present sodium phosphate composition is safe and effective and implies that a preferred embodiment is to use the reduced dosage of sodium phosphate whether it is 30 cc liquid or the equivalent in coated powder. The coated powder has some advantages over the liquid which include storage, taste and side effects other than trouble drinking.

TABLE 1

PATIENT QUESTIONNAIRE RESULTS

|  | Liquid Phospho-Soda 2 × 45 cc GROUP #1 | Liquid Phospho-Soda 2 × 30 cc GROUP #2 | Powder Phospho-Soda 8 × 0.8 g DSP 8 × 3.9 g MSP GROUP #3 | Powder Phospho-Soda 8 × 0.8 g DSP 8 × 3.9 g MSP 8 × 20.0 g PEG GROUP #4 |
|---|---|---|---|---|
| Trouble Preparing | 1 | 2 | 2 | 4 |
| Trouble Drinking | 9 | 3 | 13 | 11 |
| Nausea | 13 | 4 | 2 | 5 |
| Vomiting | 3 | — | — | — |
| Abdominal Bloating | 13 | 4 | 6 | 9 |
| Abdominal Cramps | 7 | 9 | — | 7 |
| Anal Irritation | 16 | 6 | 6 | 9 |
| Weakness or Fainting Feeling | 10 | 1 | 1 | 3 |
|  | 72 | 29 | 30 | 48 |

NONE = 0
MILD = 1
MODERATE = 2
SEVERE = 3

TABLE 2

COLON CLEANSING RESULTS

|  | GROUP #1 | GROUP #2 | GROUP #3 | GROUP #4 |
|---|---|---|---|---|
| Excellent | 7 | 5 | 4 | 5 |
| Good | 6 | 8 | 4 | 9 |
| Good to Fair | 0 | 0 | 1 | 0 |
| Fair | 1 | 0 | 2 | 1 |
| Poor | 0 | 2 | 0 | 0 |

TABLE 3

PHOSPHORUS

|  | GROUP #1 | GROUP #2 | GROUP #3 | GROUP #4 |
|---|---|---|---|---|
|  | 6.1 | 4.0 | 1.8 | 2.2 |
|  | 3.1 | 3.2 | 3.0 | 2.5 |
|  | 3.8 | 0.8 | 2.3 | 2.4 |
|  | 3.6 | 2.2 | 2.2 | 1.1 |
|  | 4.8 | 3.1 | 2.7 | 3.7 |
|  | 4.6 | 3.6 | 2.6 | 2.0 |
|  | 3.3 | 0.4 | 3.5 | 1.6 |
|  | 3.0 | 1.2 | 1.0 | 2.4 |
|  | 3.5 | 2.4 | 2.7 | 2.6 |
|  | 4.2 | 2.5 | 3.0 | 3.1 |
|  | 3.3 | 2.7 | 1.8 | 1.5 |
|  | 2.8 | 2.3 |  | 2.0 |
|  | 2.0 | 3.1 |  | 3.5 |
|  | 1.5 |  |  | 1.0 |
| Average | 3.543 | 2.423 | 2.418 | 2.257 |
| STD | 1.159 | 1.071 | 0.698 | 0.814 |

TABLE 4

SODIUM

|  | GROUP #1 | GROUP #2 | GROUP #3 | GROUP #4 |
|---|---|---|---|---|
|  | 1.0 | −3.0 | 5.0 | 1.0 |
|  | 1.0 | 3.0 | 24.0 | 0.0 |
|  | 7.0 | 3.0 | 0.0 | 4.0 |
|  | 1.0 | 1.0 | 3.0 | 0.0 |
|  | 2.0 | 1.0 | −3.0 | −1.0 |
|  | 8.0 | −3.0 | 0.0 | 0.0 |
|  | 6.0 | 0.0 | 1.0 | 2.0 |
|  | 3.0 | 2.0 | 2.0 | 1.0 |
|  | 1.0 | −1.0 | 0.0 | 4.0 |
|  | 6.0 | 0.0 | 2.0 | 4.0 |
|  | 5.0 | 0.0 | 1.0 | 0.0 |
|  | 2.0 | 0.0 | 1.0 | 4.0 |
|  | 0.0 | 1.0 |  | 4.0 |
|  | 7.0 |  |  | 3.0 |
| Average | 3.571 | 0.308 | 3.000 | 1.857 |
| STD | 2.793 | 1.888 | 7.195 | 1.964 |

TABLE 5

CALCIUM

|  | GROUP #1 | GROUP #2 | GROUP #3 | GROUP #4 |
|---|---|---|---|---|
|  | −0.4 | −0.3 | −0.6 | 0.2 |
|  | −0.1 | 0.1 | 0.1 | −0.2 |
|  | 0.3 | −0.8 | 0.2 | −0.9 |
|  | −0.7 | −0.6 | −0.3 | −0.3 |
|  | −0.7 | 0.0 | −0.4 | −0.5 |
|  | −0.3 | −1.0 | −0.1 | −2.0 |
|  | −1.0 | −1.1 | −0.2 | −0.1 |
|  | −0.7 | −0.1 | −0.8 | 0.3 |
|  | −0.2 | −0.7 | 0.1 | 0.2 |
|  | −0.3 | −0.2 | −0.8 | 0.1 |
|  | 0.1 | −0.5 | −0.3 | −0.3 |
|  | −0.7 | −0.1 | 0.0 | −1.5 |
|  | −0.8 | 0.7 |  | 0.4 |
|  | −0.8 |  |  | −0.2 |
| Average | −0.450 | −0.462 | −0.258 | −0.343 |
| STD | 0.382 | 0.391 | 0.349 | 0.722 |

TABLE 6

POTASSIUM

|  | GROUP #1 | GROUP #2 | GROUP #3 | GROUP #4 |
|---|---|---|---|---|
|  | −0.5 | −1.3 | −1.6 | −0.5 |
|  | 0.0 | −0.5 | −0.2 | −0.7 |
|  | −0.4 | −0.7 | −0.6 | −0.1 |
|  | −0.1 | −0.5 | −0.5 | 0.2 |
|  | −0.4 | −1.2 | −0.5 | −0.6 |
|  | −0.3 | −0.9 | −0.6 | 0.1 |
|  | −0.4 | −0.3 | −0.1 | 0.0 |
|  | −0.8 | −0.1 | 0.5 | −0.1 |
|  | −0.1 | −0.2 | −0.4 | 0.0 |
|  | −0.3 | −0.2 | −0.7 | −0.4 |
|  | −0.3 | 0.0 | −0.8 | −0.3 |
|  | −0.1 | −0.1 | −0.6 | −1.2 |
|  | −0.8 | −0.1 |  | −0.4 |
|  | 0.2 |  |  | −0.8 |
| Average | −0.307 | −0.469 | −0.592 | −0.343 |
| STD | 0.281 | 0.435 | 0.391 | 0.386 |

TABLE 7

NUMBER OF INCREASES AND DECREASES FOR EACH TEST IN EACH GROUP

| | GROUP #1 | | | GROUP #2 | | | GROUP #3 | | | GROUP #4 | | |
|---|---|---|---|---|---|---|---|---|---|---|---|---|
| | + | − | 0 | + | − | 0 | + | − | 0 | + | − | 0 |
| CHEM 7 | | | | | | | | | | | | |
| GLUCOSE | 4 | 10 | | 5 | 9 | | 6 | 6 | | 4 | 10 | |
| BUN | | 13 | 1 | 2 | 12 | | 1 | 11 | | 2 | 12 | |
| CREATINE | 2 | 3 | 9 | 2 | 8 | 4 | 1 | 6 | 5 | 1 | 11 | 2 |
| CHLORIDE | 7 | 6 | 1 | 6 | 7 | 1 | 3 | 9 | | 5 | 6 | 3 |
| CO2 | 4 | 10 | | 6 | 8 | | 5 | 7 | | 4 | 8 | 2 |
| CHEM PROFILE | | | | | | | | | | | | |
| URIC ACID | 9 | 4 | 1 | 4 | 8 | 1 | 7 | 4 | 1 | 11 | 3 | |
| TOTAL PROTEIN | 8 | 4 | 2 | 8 | 5 | | 7 | 3 | 2 | 9 | 3 | 2 |
| ALBUMIN | 5 | 6 | 3 | 7 | 4 | 2 | 5 | 3 | 4 | 9 | 3 | 2 |
| GLOBULIN | 10 | 1 | 3 | 7 | 2 | 4 | 8 | 2 | 2 | 6 | 6 | 2 |
| A:G RATIO | 2 | 10 | 2 | 3 | 7 | 3 | 4 | 2 | 6 | 8 | 5 | 1 |
| CHOLESTEROL | 6 | 8 | | 7 | 4 | 2 | 6 | 6 | | 8 | 6 | |
| TRIGLYCERIDE | 5 | 9 | | 1 | 11 | 1 | 8 | 4 | | 5 | 8 | 1 |
| BILIRUBIN, DIRECT | 4 | | 10 | 4 | 1 | 8 | 3 | 1 | 8 | 4 | | 10 |
| BILIRUBIN, TOTAL | 9 | 4 | 1 | 9 | 3 | 1 | 7 | 4 | 1 | 9 | 3 | 2 |
| CK | 4 | 9 | 1 | 6 | 6 | 1 | 8 | 3 | 1 | 10 | 2 | 2 |
| AST (SGOT) | 7 | 5 | 2 | 7 | 5 | 1 | 6 | 5 | 1 | 11 | 2 | 1 |
| LD | 7 | 7 | | 9 | 3 | 1 | 5 | 7 | | 12 | 2 | |
| ALT (SGOT) | 7 | 5 | 2 | 5 | 6 | 2 | 7 | 4 | 1 | 6 | 5 | 3 |
| ALP | 8 | 4 | 2 | 8 | 4 | 1 | 3 | 8 | 1 | 7 | 4 | 3 |

We claim:

1. A sodium phosphate composition which can be suspended in water to form a bowel cleansing suspension, comprising particulate monobasic sodium phosphate and particulate dibasic sodium phosphate, wherein said particulate monobasic sodium phosphate and particulate dibasic sodium phosphate are coated with at least one edible film forming polymer.

2. The composition according to claim 1, wherein said monobasic sodium phosphate and dibasic sodium phosphate are in the form of free flowing powders or crystals.

3. The composition according to claim 1, wherein said monobasic sodium phosphate and dibasic sodium phosphate are in the form of controlled release beads.

4. The composition according to claim 1, further comprising at least one additional substance selected from the group consisting of pharmaceutically acceptable fillers, dyes, and fragrances.

5. The composition according to claim 1, wherein said edible film forming polymer is hyroxypropylmethyl cellulose.

6. The composition according to claim 1, wherein the amount of monobasic sodium phosphate and dibasic sodium phosphate produces between 200–1000 Mosmols per dose.

7. The composition according to claim 2, wherein said powders or crystals have a particle size range between 10–200 mesh.

8. The composition according to claim 1, wherein said monobasic sodium phosphate and dibasic sodium phosphate are coated with 10.0%±7.0% hydroxypropylmethyl cellulose and 1–10% w/w paraffin.

9. A method for producing a coated phosphate powder or crystal comprising the steps of:
  a) placing uncoated phosphate powder or crystals in a fluidbed processing bowl,
  b) suspending the phosphate powder or crystals in a heated inert gas stream to heat the phosphate powder or crystals,
  c) applying a coating solution to said phosphate powder or crystals to produce a coated phosphate powder or crystals,
  d) drying the coated phosphate powder or crystals, and
  e) thereafter applying a coating of melted paraffin on said coated phosphate powder or crystals to produce a coated sodium phosphate powder or crystal composition.

10. The method according to claim 9, wherein said uncoated phosphate powder is selected from the group consisting of monobasic sodium phosphate, dibasic sodium phosphate and a mixture of monobasic sodium phosphate and dibasic sodium phosphate.

11. The method according to claim 9, wherein said coating solution is a solution of hydroxypropylmethyl cellulose which contains 10.0% ±2.0% hydroxypropylmethyl cellulose.

12. The method according to claim 9, further comprising classifying said coated sodium phosphate composition by passing said product through a 10 mesh screen to remove any oversized particles.

13. The method according to claim 9, wherein said coated phosphate is dried to a moisture level of less than 1.0% $H_2O$.

14. The method according to claim 9, wherein in step b) said phosphate is suspended in a heated inert gas stream of 500–900 CFM at a temperature between 80–120° C. to heat the phosphate to a temperature of 55–65° C.

15. The method according to claim 9, wherein said paraffin is applied using atomized air heated to a temperature of 100°±15° C.

16. The method according to claim 9, wherein said coating solution is applied by a controlled pumping system through an air atomized nozzle.

17. A bowel cleansing composition comprising monobasic sodium phosphate and dibasic sodium phosphate suspended in a aqueous solution, wherein said monobasic sodium phosphate and dibasic sodium phosphate are in particulate form and are coated with a film forming polymer.

18. A dry sodium phosphate composition, comprising free flowing monobasic sodium phosphate and dibasic sodium phosphate powders or crystals coated with a film forming polymer.

19. The pharmaceutical composition according to claim 18, wherein said film forming polymer is hydroxypropylmethyl cellulose.

20. The composition according to claim 18, further comprising at least one substance selected from the group consisting of pharmaceutically acceptable fillers, dyes, flavors and fragrances.

21. The composition according to claim 1, wherein said edible film forming polymer reduces electrolyte shift by binding sodium and phosphate ions.

22. The composition according to claim 1, wherein said edible film forming polymer forms at least one layer which blocks the migration of sodium and/or potassium ions.

23. The composition according to claim 1, wherein two edible film forming polymers are present as first and second layers and said second layer blocks any pores present in said first layer.

24. The composition according to claim 1, wherein said wherein said edible film forming polymer is nonmetabolizable.

* * * * *